US007569338B1

(12) United States Patent
McDonald et al.

(10) Patent No.: US 7,569,338 B1
(45) Date of Patent: Aug. 4, 2009

(54) DIAGNOSTIC ASSAYS OF SECRETED BIOLOGICAL FLUIDS FOR DETECTION OF INFECTION AND INFLAMMATORY CONDITIONS

(75) Inventors: Thomas L. McDonald, Omaha, NE (US); Annika Weber, Omaha, NE (US)

(73) Assignee: Accuplex, LLC., Omaha, NE (US)

( * ) Notice: Subject to any disclaimer, the term of this patent is extended or adjusted under 35 U.S.C. 154(b) by 0 days.

(21) Appl. No.: 10/069,810

(22) PCT Filed: Aug. 25, 1999

(86) PCT No.: PCT/US99/19418

§ 371 (c)(1), (2), (4) Date: Jul. 9, 2002

(87) PCT Pub. No.: WO01/14580

PCT Pub. Date: Mar. 1, 2001

(51) Int. Cl.
*C12Q 1/00* (2006.01)
*G01N 33/53* (2006.01)

(52) U.S. Cl. .............................. 435/4; 435/7.1; 435/7.2; 435/7.6; 435/7.72; 435/7.94; 503/380; 503/386; 503/415

(58) Field of Classification Search .................... 435/4, 435/7.1, 7.2, 7.6, 7.72, 7.94; 503/380, 386, 503/415
See application file for complete search history.

(56) References Cited

U.S. PATENT DOCUMENTS

| 4,755,380 | A |   | 7/1988  | Grubb         |         |
|-----------|---|---|---------|---------------|---------|
| 4,952,496 | A |   | 8/1990  | Studier       |         |
| 5,227,302 | A |   | 7/1993  | Turner        |         |
| 5,536,640 | A | * | 7/1996  | Sipe et al.   | 435/7.5 |
| 5,807,684 | A |   | 9/1998  | Simmons et al.|         |
| 5,853,985 | A |   | 12/1998 | Salbaum       |         |
| 5,952,313 | A |   | 9/1999  | Carlson       |         |
| 5,958,883 | A |   | 9/1999  | Snow          |         |
| 6,004,936 | A |   | 12/1999 | Kisilevsky    |         |
| 6,013,857 | A |   | 1/2000  | Deboer        |         |

FOREIGN PATENT DOCUMENTS

| EP | 0 872 558 A   | 10/1998 |
| EP | 1 067 194     | 1/2001  |
| WO | WO/95/21625   | 8/1995  |
| WO | PCT/JP96/02219| 7/1996  |
| WO | WO/97/04317   | 2/1997  |
| WO | WO/97/06184   | 2/1997  |
| WO | WO/98/03206   | 1/1998  |
| WO | WO/98/40506   | 9/1998  |
| WO | WO/99/18227   | 4/1999  |
| WO | WO/01/14580   | 3/2001  |
| WO | WO/01/31006   | 3/2001  |

OTHER PUBLICATIONS

Jacobsen et al. Kinetics of Local and systemic isoforms or serum amyloid A in bovine mastitis milk. Veterinary Immunology & Immunopathology 104 (2005) 21-31.*
Bowie, "Deciphering the Message in Protein Sequences: Tolerance to Amino Acid Substitutions", Science 247:1306-1310 (1990).
Kluve-Beckerman, "Nonexpression of the Human Serum Amyloid A Three (SAA3) Gene", DNA and Cell Biology, 10(9):651-661 (1991).
McDonald, "A monoclonal antibody sandwich immunoassay for serum amyloid A (SAA) protein", J. of Immunolog. Methods, 144:149-155 (1991).
Pedersen, "The biology of eukaryotic promoter prediction-a review", Computers & Chemistry 23:191-207 (1999).
Sack, "The human serum amyloid A (SAA)-encoding gene GSAA1:nucleotide sequence and possible autocrine-collagenase-inducer function", Gene, 84:509-515 (1989).
Skolnick, "From Genes to Protein Structure and Function: Novel Applications for Computational Approaches in the Genomic Area", TIBTECH 18:34-39 (2000).
Bowie, James U., et al., "Deciphering the Message in Protein Sequences: Tolerance to Amino Acid Substitutions", Science 247:1306-10 (1990).
Skolnick, Jeffrey et al., "From genes to protein structure and function: novel applications of computational approaches in the genomic era", TIBTECH 18:34-39 (2000).
Bauman et al., "The acute phase response", IT Review, 1994 Elsevier Science Ltd, 0167-5699/94.
Benson et al., "A unique insertion in the primary structure of bovie amyloid AA protein", J. Lab ClinMed, vol. 113, pp. 67-72, 1989.
Hulten et al., "The acute phase serum amyloid A protein (SAA) in the horse: isolation and characterization of three isoforms", Veterinary Immunology and Immunopathology 57, 215-227, 1997.
Jensen et al., "Regulation of serum amyloid A protein expression during the actue-phase response", Biochem J. 334, 489-503, 1998.
Kho et al., GenBank Submission AAF77630, serum amyloid A protein, (Bos Taurus).
Kho et al., Rapid Communication: Cloning of bovine serum amyloid A# cDNA1, American Society of Animal Science, May 19, 2000.
Kho et al., "Cloning and characterization of involution-specific genes from the bovine mammary gland" Database EMBL 'Online! Database accession No. AF160867; Jun. 30, 2000.
Kluve-Beckerman et al., "Human sermu amyloid A—Three Hepatic mRNAs and the corresponding proteins in one person", The Journal of Clinical Investigation, vol. 82, pp. 1670-1675, 1988.

(Continued)

*Primary Examiner*—Mark L Shibuya
*Assistant Examiner*—Pensee T Do
(74) *Attorney, Agent, or Firm*—McKee, Voorhees & Sease, P.L.C.

(57) ABSTRACT

A rapid and convenient method for detecting inflammatory conditions in breast tissue, such as those associated with mastitis, is described. The method comprises measuring the presence and quantity of Serum Amyloid A (SAA) in milk samples obtained from the breast tissue. The amount of SAA present in the milk is positively correlated with the level of inflammation of the breast tissue, and can localize the inflammation to a particular region of the breast organ, such as a specific quadrant of a cow's udder. Test kits and their use in the method are also described.

10 Claims, No Drawings

OTHER PUBLICATIONS

Kluve-Beckerman et al., "Primary structures of dog and cat amyloid A proteins: comparison to Human AA", Comp. Biochem Physiol. B, vol. 94, pp. 175-183, 1989.
Kluve-Beckerman et al., "Sequence Analysis of a Third Human SAA gene", Database CAPLUS on STN, meeting abstract, 1991.
Larson et al., "Human serum amyloid A3 peptide enhances intestinal MUC3 expression and inhibits EPEC adherence", pp. 531-540, Biochemical and Biophysical Research Communications 300, Elsevier Science, 2002.
Larson et al., "Induction of human mammary-associated serum amyloid A3 expression by prolactin or lipopolysaccharide", pp. 1030-1037, Biochemical and Biophysical Research Communications 301, Elsevier Science, 2003.
Liang et al., "Amino terminal region of acute phase, but not constitutive, serum amyloid A (apoSAA) specifically binds and transports cholesterol into aortic smooth muscle and HepG2 cells", Journal of Lipid Research 37:2109-2116, 1996.
Liepnieks et al., "The primary structure of serum amyloid A protein in the rabbit: Comparison with serum amyloid A proteins in other species", J Lab Clin Med, 118(6):570-576, 1991.
McDonald et al., "Elevated extrahepatic expression and secretion of mammary-associate serum amyloid A3 (M-SAA3) into colostrums", Veterinary Immunology and Immunopathology 6528, 2001.
Malle, E., "Human serum amyloid A (SAA) protein: a prominent acute-phase reactant for clinical practice", European Journal of Clinical Investigation 26:427-435, 1996.
Marhaug et al., "Mink serum amyloid A protein. Expression and primary structure based on cDNA", J. Biol. Chem., vol. 265, 10049-10054, 1990.
Migita, K., et al., "Serum Amyloid A Protein Induces Production of Matrix Metalloproteinases by Human Synovial Fibroblasts", Laboratory Investigation, 78(5): 535-539, 1998.
Mitchell et al., "Serum Amyloid A SAA3 produced by rabbit synovial fibroblasts treated with phorbol esters or interleukin 1 induces synthesis of collagenase and is neutralized with specific antiserum", Journal of Clinical Investigation, vol. 87, No. 4, pp. 1177-1185, XP000992756, 1991.
Mitchell et al., "The acute phase reactant serum amyloid A (SAA3) is a novel substrate for digradation by the metalloproteinases collagenase and stromelysin", Biochem et Biophysica Acta., 1156:245-254, 1993.
Patel, H., "Human Serum Amyloid A has Cytokine-like Properties", Scand. J. Immunol., 48:410-418, 1998.
Peristeris, P., "Effects of serum amyloid A protein on lymphocytes, HeLa, and MRC5 cells in culture", Biochem. Cell Biol. 67:365-370, 1989.
Rossevatn, et al., "The complete amino acid sequence of bovine serum amyloid protein A (SAA) and of subspecies of the tissue-deposited amyloid fibril protein A", Scand. J. Immunol., 35(2), 217-24, 1992.
Rygg et al., "In vitro evaluation of an enhanced Human Serum Amyloid A (SAA) Promoter-regulated soluble TNF Receptor Fusion Protein for Anti-inflammatory Gene Therapy", Scand J Immunol, 2001.
Sellar et al., "Oganization of the Region Encompassing the Human Serum Amyloid A (SAA) Gene Famil on Chromosome 11", Genomics, vol. 23, pp. 492-495, 1994.
Sletten et al., "The amino acid sequence of an amyloid fibril protein AA isolated from the horse", Scand. J. Immunol. 26, 79-84, 1987.
Sletten et al., "The primary structure of equine serum amyloid A (SAA) protein", Scand. J. Immunol., vol. 30, pp. 117-122, 1989.
Smith, J., et al., "Comparison of Serum Amyloid A and C-Reactive Protein as Indicators of Lung Inflammation in Corticosteroid Treated and Non-Corticosteroid Treated Cystic Fibrosis Patients", Journal of Clinical Laboratory Analysis 6:219-224, 1992.

Smith, J. et al., "Use of Ethanol-Eluted Hydrophobic Interaction Chromatography in the Purification of Serum Amyloid A", Protein Expression and Purification 2:158-161, 1991.
Smith, J. et al., "Production of serum amyloid A and C-reactive protein by HepG2 cells stimulated with combinations of cytokines or monocyte conditioned media: the effects of prednisolone", Clin. Exp. Immunol. 783, 1992.
Steel, et al., "The major acute phase reactant: C-reactive protein, serum amyloid P component and serum and amyloid A protein", Review, Elsevier Science Ltd., 0167-5699/94.
Steel, et al., "Expression and Regulation of Constitutive and Acute Phase Serum Amyloid A mRnas in Hepatic and Non-Hepatic Cells Lines", Blackwell Science Ltd., Scandinavian Journal of Immunology, 44:493-500, 1996.
Syversen et al., "The primary structure of serum amyloid A protein in the sheep, comparison with serum amyloid A in other species", Scand. J. Immuno., vol. 39, pp. 88-94, 1994.
Thompson, et al. The value of acute phase protein measurements in clinical practice, Ann Clin Biochem 29:123-131, 1992.
Ulhar, C., "Evolution of the Serum Amyloid A (SAA) Protein Superfamily", Genomics, 19:228-235, 1994.
Waalen et al., "The primary structure of amyloid fibril protein AA in endotoxin-induced amyloid", European Journal of Biochem, vol. 104, p. 407-412, 1980.
Zimlichman, S., "Serum amyloid A, an acute phase protein, inhibits platelet activation, Serum Amyloid A and platelet activation", 116(2):180-186.
Newstead, D.F. "Acceptable levels of bovine immunoglobulin in colostrums testing" New Zealand Journal of Dairy science and Technology, vol. 6, No. 2, 1971, p. 2, XP008036075.
Nielsen, B.H. et al. "Acute phase protein concentrations in serum and milk from healty cows, cows with clinical mastitis and cows with extramammary inflammatory conditions" The Veterinary Record. Mar. 20, 2004, vol. 154, No. 12, pp. 361-365, ISSN: 0042-4900.
Schrödl, W., et al. "C-reaction protein as a new parameter of mastitis's!" Tierarztlich Praxis. vol. 23, No. 4, Aug. 1995, pp. 337-341, XP008036085, ISSN: 0303-6286.
Simcha, Urieli-Shoval et al. "Widespread expression of serum amyloid A in histologically normal human tissues: predominant localization to the epithelium" Journal of Histochemistry and Cytochemistry, vol. 46, No. 12, Dec. 1998, pp. 1377-1384, XP002298394, ISSN: 0022-1554.
Sipe, J.D. et al. "Direct binding enzyme-linked immunosorbent assay (Elisa) for serum amyloid A (SAA)" Journal of Immunological Methods, Elsevier Science, Publishers B.V. Amsterdam, NL, vol. 125, No. ½, 1989, pp. 125-135, XP002018648, ISSN: 0022-1759.
Hirvonen, et al., "Acute Phase Response in Heifers with Experimentally Induced Mastitis", J. of Dairy Res. 63:351-360 (1996).
Huszenicza, et al., "Diagnostic Value of Certain Mastitis Markers in Following Up the Clinical and Bacteriological Changes in Pharmacotherapeutic Studies", Acta Veterinaria Hungarcia 45(4):409-416 (1997).
McDonald, et al., "A Monoclonal Antibody Sandwich Immunoassay for Serum Amyloid A (SAA) Protein", J. Immun. Methods 144:149-155 (1991).
Satoh, et al., "Sandwich Enzyme-Linked Immunosorbent Assay for Quantitative Measurement of Serum Amyloid A Protein in Horses", Am. J. Vet Res. 56(10):1286-1291.
Taktak, et al., "A Solid Phase Enzyme Immunoassay for Serum Amyloid A (SAA) Protein", J. Immun. Methods 136:11-16 (1991).
Wilkins, et al., "Rapid Automated Enzyme Immunoassay of Serum Amyloid A", Clinical Chemistry 40(7):1284-1290 (1994).
Zank, et al., "Assessment of Subacute Mammary Inflammation by Soluble Biomarkers in Comparison to Somatic Cell Counts in Quarter Milk Samples from Dairy Cows", J.Vet. Med. 45:41-51 (1998).

* cited by examiner

SEQUENCE LISTING

```
<160> NUMBER OF SEQ ID NOS: 15

<210> SEQ ID NO 1
<211> LENGTH: 20
<212> TYPE: PRT
<213> ORGANISM: Bos taurus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1

Met Trp Xaa Thr Phe Leu Lys Glu Ala Gly Gln Gly Ala Lys Asp Met
1               5                   10                  15
```

```
Trp Arg Ala Tyr
            20

<210> SEQ ID NO 2
<211> LENGTH: 27
<212> TYPE: PRT
<213> ORGANISM: Bos taurus
<220> FEATURE:
<221> NAME/KEY: misc_feature
<222> LOCATION: (1)..(2)
<223> OTHER INFORMATION: Xaa can be any naturally occurring amino acid

<400> SEQUENCE: 2

Xaa Xaa Trp Met Ser Phe Phe Gly Glu Ala Tyr Glu Gly Ala Lys Asp
1               5                   10                  15

Met Trp Arg Ala Tyr Ser Asp Met Arg Glu Ala
            20                  25

<210> SEQ ID NO 3
<211> LENGTH: 27
<212> TYPE: PRT
<213> ORGANISM: Homo sapiens

<400> SEQUENCE: 3

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala
            20                  25

<210> SEQ ID NO 4
<211> LENGTH: 27
<212> TYPE: PRT
<213> ORGANISM: Homo sapiens

<400> SEQUENCE: 4

Gln Gly Trp Leu Thr Phe Leu Lys Ala Ala Gly Gln Gly Ala Lys Asp
1               5                   10                  15

Met Trp Arg Ala Tyr Ser Asp Met Lys Glu Ala
            20                  25

<210> SEQ ID NO 5
<211> LENGTH: 27
<212> TYPE: PRT
<213> ORGANISM: Oryctolagus cuniculus

<400> SEQUENCE: 5

Gln Arg Trp Phe Ser Phe Ile Gly Glu Ala Thr Gln Gly Ala Trp Asp
1               5                   10                  15

Met Trp Arg Ala Tyr Ser Asp Met Arg Glu Ala
            20                  25

<210> SEQ ID NO 6
<211> LENGTH: 27
<212> TYPE: PRT
<213> ORGANISM: Oryctolagus cuniculus

<400> SEQUENCE: 6

Arg Glu Trp Leu Thr Phe Leu Lys Glu Ala Gly Gln Gly Ala Lys Asp
1               5                   10                  15

Met Trp Arg Ala Tyr Ser Asp Met Lys Glu Ala
            20                  25

<210> SEQ ID NO 7
```

```
<211> LENGTH: 27
<212> TYPE: PRT
<213> ORGANISM: Mus musculus

<400> SEQUENCE: 7

Gly Gly Phe Phe Ser Phe Val His Glu Ala Phe Gln Gly Ala Gly Asp
1               5                   10                  15

Met Trp Arg Ala Tyr Thr Asp Met Lys Glu Ala
            20                  25

<210> SEQ ID NO 8
<211> LENGTH: 27
<212> TYPE: PRT
<213> ORGANISM: Mus musculus

<400> SEQUENCE: 8

Gln Arg Trp Val Gln Phe Met Lys Glu Ala Gly Gln Gly Ser Arg Asp
1               5                   10                  15

Met Trp Arg Ala Tyr Ser Asp Met Lys Lys Ala
            20                  25

<210> SEQ ID NO 9
<211> LENGTH: 27
<212> TYPE: PRT
<213> ORGANISM: Mesocricetus auratus

<400> SEQUENCE: 9

Gln Arg Trp Phe Gln Phe Met Lys Glu Ala Gly Gln Gly Thr Arg Asp
1               5                   10                  15

Met Trp Arg Ala Tyr Thr Asp Met Arg Glu Ala
            20                  25

<210> SEQ ID NO 10
<211> LENGTH: 27
<212> TYPE: PRT
<213> ORGANISM: Mesocricetus auratus

<400> SEQUENCE: 10

Gln Arg Trp Phe Gln Phe Met Lys Glu Ala Gly Gln Gly Ser Thr Asp
1               5                   10                  15

Met Trp Arg Ala Tyr Ser Asp Met Arg Glu Ala
            20                  25

<210> SEQ ID NO 11
<211> LENGTH: 27
<212> TYPE: PRT
<213> ORGANISM: equus caballus
<220> FEATURE:
<221> NAME/KEY: misc_feature
<222> LOCATION: (1)..(2)
<223> OTHER INFORMATION: Xaa can be any naturally occurring amino acid

<400> SEQUENCE: 11

Xaa Xaa Leu Leu Ser Phe Leu Gly Glu Ala Ala Arg Gly Thr Trp Met
1               5                   10                  15

Asp Leu Arg Ala Thr Asn Asp Met Arg Glu Ala
            20                  25

<210> SEQ ID NO 12
<211> LENGTH: 13
<212> TYPE: PRT
<213> ORGANISM: equus caballus

<400> SEQUENCE: 12
```

-continued

```
Arg Glu Leu Lys Thr Phe Leu Lys Glu Ala Gly Gln Gly
1               5                   10

<210> SEQ ID NO 13
<211> LENGTH: 10
<212> TYPE: PRT
<213> ORGANISM: Sus scrofa

<400> SEQUENCE: 13

Trp Leu Leu Thr Phe Leu Lys Glu Ala Gly
1               5                   10

<210> SEQ ID NO 14
<211> LENGTH: 27
<212> TYPE: PRT
<213> ORGANISM: Mustela vison
<220> FEATURE:
<221> NAME/KEY: misc_feature
<222> LOCATION: (2)..(2)
<223> OTHER INFORMATION: Xaa can be any naturally occurring amino acid

<400> SEQUENCE: 14

Gln Xaa Trp Tyr Ser Phe Ile Gly Glu Ala Ala Gln Gly Ala Trp Asp
1               5                   10                  15

Met Tyr Arg Ala Tyr Ser Asp Met Ile Glu Ala
            20                  25

<210> SEQ ID NO 15
<211> LENGTH: 27
<212> TYPE: PRT
<213> ORGANISM: canis major
<220> FEATURE:
<221> NAME/KEY: misc_feature
<222> LOCATION: (2)..(2)
<223> OTHER INFORMATION: Xaa can be any naturally occurring amino acid

<400> SEQUENCE: 15

Gln Xaa Trp Tyr Ser Phe Val Gly Glu Ala Ala Gln Gly Ala Trp Asp
1               5                   10                  15

Met Leu Arg Ala Tyr Ser Asp Met Arg Glu Ala
            20                  25
```

US 7,569,338 B1

DIAGNOSTIC ASSAYS OF SECRETED BIOLOGICAL FLUIDS FOR DETECTION OF INFECTION AND INFLAMMATORY CONDITIONS

FIELD OF THE INVENTION

The present invention relates generally to the field of diagnostics. In particular, the invention provides a method for diagnosing infection and other inflammatory conditions by measuring the presence of Serum Amyloid A in a secreted biological fluid. The invention further provides a test kit for use in the method.

BACKGROUND OF THE INVENTION

Several scientific or patent publications are referenced in this patent application to describe the state of the art to which the invention pertains. Each of these publications is incorporated by reference herein, in its entirety.

Mammals respond to tissue injury, trauma or infection by executing a complex series of biological reactions in an effort to prevent further tissue damage, to initiate repair of damaged tissue, and to isolate and destroy infective organisms. This process is referred to as the inflammatory response, the early and intermediate stages of which are referred to as the acute phase response.

The acute phase response involves a wide variety of mediators, including cytokines, interleukins and tumor necrosis factor. It also involves a radical alteration in the biosynthetic profile of the liver. Under normal circumstances, the liver synthesizes a range of plasma proteins at steady state concentrations. Some of these proteins, the "acute phase" proteins are induced in the inflammatory response to a level many times greater than levels found under normal conditions. Acute phase proteins are reviewed by Steel & Whitehead (Immunology Today 15: 81-87, 1994).

One of the massively induced acute phase proteins is Serum Amyloid A (SAA). SAA actually comprises a family of polymorphic proteins encoded by many genes in a number of mammalian species. SAAs are small apolipoproteins that accumulate and associate rapidly with high-density lipoprotein 3 (HDL3) during the acute phase of the inflammatory response. Most SAAs are induced in response to inflammation; however, certain SAAs (e.g., human SAA4) appear to be constitutively expressed or minimally induced in the inflammatory response.

SAAs are regulated transcriptionally and post transcriptionally, though transcriptional regulation appears to predominate. SAA mRNA levels have been observed to increase up to 1,000 fold in the hours following an inflammatory stimulus. Likewise, plasma concentrations of SAA protein have been shown to increase as much as 1,000 fold, to levels approaching 1 mg/ml, for short periods following an inflammatory stimulus.

The massive increase in SAA plasma levels in response to both infective and non-infective inflammatory stimuli has led to its use as a diagnostic marker of inflammation. Among the most effective assays are immunoassays utilizing antibodies raised in a species that does not produce detectable amounts of SAA. For instance, McDonald et al. (J. Immunol. Meth. 144: 149-155, 1991) describe an antibody sandwich assay using two purified rat monoclonal antibodies raised against human SAA. Immunoassays utilizing these antibodies were demonstrated to be reliable and sensitive, and do not require denaturation of the specimen prior to assay (McDonald et al., 1991, supra). Similarly, Satoh et al. (Am J. Vet. Res. 56: 1286-1291, 1995) describe an ELISA assay for measuring SAA levels in horse serum using rabbit anti-horse SAA antibodies. Though effective, these and similar immunoassays are invasive in that they require a blood sample. Moreover, they may not be appropriate or effective for early detection of localized inflammation, which is common in connection with a variety of infectious and non-infectious tissue trauma.

One excellent example of a non-systemic inflammatory-related disease of great economic importance to the dairy industry is mastitis. Mastitis is generally regarded as an inflammation of the mammary gland. The disease can affect any mammal, but is most economically significant in dairy heifers and cows. Mastitis usually results from colonization of the mammary gland by pathogenic bacteria. However, physical injuries or local mechanical or chemical stresses in the udder can also trigger a local inflammation cascade without the involvement of any primary bacterial infection (sometimes referred to as sterile mastitis).

Mastitis can be expressed at clinical or subclinical levels, and may be localized to only a portion of the udder. Subclinical or localized mastitis is economically damaging because it often remains undetected and untreated, yet results in decreased milk production. Accordingly, it is important in the early diagnosis of mastitis to be able to detect infection before clinical symptoms arise, and to be able to localize the infection to specific regions of the udder.

Current clinical laboratory methods used for the diagnosis of mastitis include estimation of somatic cell counts (SCC), various electrolyte levels, and soluble proteins, such as lactate dehydrogenase (LDH) and N-acetyl-β-D glucosamidase (NAG), in milk samples, all of which reflect a breakdown in the blood-milk barrier due to the inflammatory response caused by the infection. Certain of these parameters, e.g., SCC and electrolyte estimates, are unable to differentiate infected from uninfected regions of the udder (Zank & Slatterer, J. Vet. Med. 45: 41-51, 1998), while others, e.g., LDH and NAG detection, may not be sufficiently sensitive for very early diagnosis. Accordingly, new indicators that are highly predictive of the onset of mastitis infection at an early stage are needed.

SUMMARY OF THE INVENTION

According to one aspect of the invention, a rapid and convenient method for detecting an inflammatory response in a breast of a lactating mammal is provided. The method comprises measuring the presence or amount of a Serum Amyloid A (SAA) protein or mRNA encoding the protein, in a sample of milk obtained from the breast, the amount of the SAA protein or mRNA present in the sample being positively correlated with the inflammatory response. In a preferred embodiment, the inflammatory response reflects mastitis in the animal, caused either by infection with a pathogenic organism or by a non-infective stress or trauma to the breast tissue.

The SAA detected and quantified in the milk preferably comprises one or more inflammation-responsive isoforms of SAA. Specifically, the SAA comprises an amino acid sequence selected from the group consisting of SEQ ID NOS: 1-15.

In one embodiment, the method comprises measuring the amount of SAA protein in the milk sample. Preferably, the amount of SAA protein is measured using an immunological assay with antibodies immunologically specific for one or more isoforms of SAA. Most preferably, the immunological assay is an ELISA assay.

Another embodiment comprises measuring the amount of SAA mRNA in the milk sample. Preferably, the amount of SAA mRNA is measured using a hybridization assay with nucleic acid molecules complementary to the SAA mRNA.

The methods of the invention may be adapted for a variety of purposes. In one embodiment, a method is provided for evaluating a therapeutic agent or treatment for its ability to decrease or increase the inflammatory response in breast tissue. In this embodiment, the therapeutic agent or treatment is applied to a test subject. A milk sample is taken from the test subject and from a control subject that did not receive the agent or treatment. SAA levels in the test sample and the control sample are compared. An increase in SAA amount in the test sample as compared with the control sample indicates that the therapeutic agent has a detrimental side effect of increasing inflammation in the breast tissue. A decrease in SAA in the test sample as compared with the control sample indicates that the therapeutic agent or treatment decreases inflammation in the breast tissue.

In another embodiment, the methods of the invention are employed to monitor milk quality. Samples of milk batches are assayed for the presence and amount of SAA, and compared to a sample accepted as a known standard for a predetermined milk quality. The comparative amount of SAA in the test sample versus the standard is used to assign a milk quality rating to the batch of milk.

In another embodiment, the methods of the invention are used to determine the presence and amount of colostrum in a milk sample. This embodiment makes use of the inventors' discovery that SAA levels are elevated in colostrum, but not in normal milk. Test samples of milk batches suspected of containing colostrum are assayed for SAA (preferably a colostrum-specific SAA) and compared to a sample known to be colostrum-free. The comparative amount of SAA in the test sample versus the control sample is determinative of whether the test sample is tainted with colostrum.

According to another aspect of the invention diagnostic kit for screening milk samples to detect inflammation in breasts of lactating mammals are provided. In one embodiment, a test kit comprises a container containing one or more antibodies immunologically specific for one or more SAA isoforms, and instructions for performing immunological assays of milk samples for SAA, using the antibodies. In another embodiment, the test kit comprises a container containing one or more nucleic acid molecules that specifically hybridizes to mRNA encoding or more SAA isoforms, and instructions for performing hybridization assays of milk samples for SAA, using the nucleic acids. These kits may further comprise at least one additional reagent for performing the immunologic or hybridization assays.

Other features and advantages of the present invention will be better understood by reference to the drawings, detailed descriptions and examples that follow.

DETAILED DESCRIPTION OF THE INVENTION

I. Definitions

Various terms relating to the methods and kits of the present invention are used hereinabove and also throughout the specification and claims.

With respect to antibodies, the term "immunologically specific" refers to antibodies that bind to one or more epitopes of a protein of interest, but which do not substantially recognize and bind other molecules in a sample containing a mixed population of antigenic biological molecules.

With respect to oligonucleotides or other single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

II. Description

Serum amyloid A (SAA) is an acute phase protein which is produced in the liver and occurs at elevated levels in the serum of mammals in response to inflammation related to tissue injury or infection. The present invention arises from the surprising discovery that elevated levels of SAA also occur in the milk of lactating females, in response to inflammatory conditions of the breast. In particular, cows with mastitis display elevated SAA levels that correlate with the severity of the infection, and that are confined to the area of the udder affected with the mastitis associated inflammation. This is believed to be the first observation of increased production of SAA in a secreted biological fluid, in response to inflammation of the tissue in which that fluid is produced.

Without being limited by any particular explanation, the SAA found in milk from inflamed breast tissue may result in part from a breakdown in the blood-milk barrier, allowing cellular material and plasma enzymes to leak into the milk. However, experimental results obtained by the inventors show that serum SAA levels in cows is independent of colostrum and whey SAA levels. In samples of colostrum, whey and serum taken from test cows, serum SAA was found to be in the range of 10 μg/ml, while in colostrum, SAA was elevated to levels in the range of 470 μg/ml (average of 5 cows). These results indicate that the source of the SAA in milk arises from an independent source in the mammary tissue, e.g., ductal epithelial cells.

The measurement of SAA levels in milk for early detection of inflammation related to mastitis is exemplified herein. However, it will be apparent to persons of skill in the art that the principles applied to SAA detection in milk to diagnose mastitis-related inflammation likewise can be applied to detection of inflammatory conditions caused by other agents, such as mechanical injury, granulomatous disease, fibrocystic disease and cancer.

Furthermore, if SAA is detected in milk as an indicator of an inflammation in the tissue from which it was secreted, it is likewise expected to be found in other biological fluids secreted from inflamed tissue. For instance, elevated SAA levels are expected to occur in urine from an infected kidney or bladder. Elevated SAA levels may also occur in saliva, sputum, sweat or tears, arising from infected oral, lung, skin or lachrymose tissues, respectively. Application of the methods described herein for early detection of inflammatory conditions of those tissues are considered within the scope of the present invention.

As one example, SAA content in sputum may be used to identify a variety of lung inflammatory conditions in a patient (human or animal), including fungal and bacterial infections of the lung, as in hypersensitive pneumonitis (e.g., Farmer's lung), viral and bacterial pneumonia, bacterial colonization and growth in Cystic Fibrosis flare (primarily caused by *Pseudomonas*), and cancer. Such application is considered particularly useful in equine veterinary applications, where unspecified or sub-clinical lung inflammations can undermine the general health of valuable horses, such as racehorses (see, e.g., Equine Veterinary Journal 21:106-109, 1989; Journal Veterinary Medical Science 55: 1011-1116, 1993).

As another example, SAA content in urine may be used to identify a variety of kidney or bladder inflammatory conditions in a patient (human or animal), including interstitial cystitis (bladder or kidney involved) and kidney transplant rejection.

Referring now to the exemplary embodiment of the invention, milk is analyzed for the presence and amount of SAA as a diagnostic test for inflammation, usually associated with mastitis. The assays of the invention comprise providing a test sample of milk from tissue suspected of being inflamed. The SAA level in the sample is measured, and preferably compared to a milk sample taken from known normal tissue. The amount of increase in SAA in the test sample as compared to the control sample is directly proportional to the level of inflammation present in the tissue from which the sample was taken.

SAA exists in several isoforms, most of which are increased in production in an inflammatory response. In accordance with the present invention, any one inflammation-responsive isoform, or a combination of isoforms, may be detected in the assay. In a preferred embodiment applicable to testing cow's milk, bovine SAA isoforms are detected. One isoform of bovine SAA has been reported to date. However, in accordance with the present invention, a new bovine SAA isoform has been identified, which is associated with colostrum and which may comprise part or all of the SAA found in milk from inflamed tissue. Accordingly, the present invention contemplates detecting one or both of these SAA isoforms in assays of cow's milk. A portion of the amino acid sequence comprising the bovine colostrum-associated SAA is set forth herein as SEQ ID NO:1. A portion of the amino acid sequence of the bovine serum SAA isoform is set forth herein as SEQ ID NO:2.

In alternative embodiments, isoforms of SAA from different species are detected (partial amino acid sequences of these isoforms are set forth herein). These include, but are not limited to, human SAA1 (SEQ ID NO:3), human SAA3 (SEQ ID NO:4), rabbit SAA1 (SEQ ID NO:5), rabbit SAA3 (SEQ ID NO:6), mouse SAA1 (SEQ ID NO:7), mouse SAA3 (SEQ ID NO:8), hamster SAA1 (SEQ ID NO:9), hamster SAA3 (SEQ ID NO: 10), horse SAA (SEQ ID NO:11), horse colostrum-associated SAA (SEQ ID NO: 12), pig colostrum-associated SAA (SEQ ID NO: 13), mink SAA1 (SEQ ID NO:14) and dog SAAa (SEQ ID NO:15).

Any assay that detects and quantifies SAA in a sample is contemplated for use in the present invention. Two categories of assays are preferred. One is an immunological assay for SAA protein and the other is a hybridization assay for mRNA encoding SAA protein. The latter assay is effective because SAA is transcriptionally regulated. Accordingly, the inflammation response comprises an increase in SAA mRNA production and a concomitant increase in protein production.

Immunological assays for SAA require antibodies immunologically specific for one or more SAA isoforms. Polyclonal or monoclonal antibodies directed toward SAA may be prepared according to standard methods. Monoclonal antibodies may be prepared according to general methods of Köhler and Milstein, following standard protocols. In a preferred embodiment, anti-SAA antibodies are raised in animals that produce little or no SAA themselves, since SAA is more immunogenic to these animals. One preferred animal source of anti-SAA antibodies is the rat. In another preferred embodiment, antibodies are prepared that react with a plurality of SAA isoforms. Such antibodies may be polyclonal or monoclonal antibodies. In a particularly preferred embodiment, antibodies such as those described by McDonald et al. (J. Immunol. Meth. 144: 149-155, 1991) are used. These antibodies, raised against human SAA, also react with a variety of SAA isoforms from other species, including bovine SAA.

A variety of immunological assays known in the art are available to detect and quantitate SAA in milk samples or samples of other secreted biological fluids. These include, but are not limited to, (1) immunoprecipitation followed by protein quantification; (2) immunoblot analysis (e.g., dot blot, Western blot) (3) radioimmune assays, (4) nephlometry, turbidometric or immunochromatographic (lateral flow) assays, and (5) enzyme-coupled assays, including ELISA and a variety of qualitative rapid tests (e.g., dip-stick and similar tests). Of these, ELISA assays are preferred for use in the invention, due to their ease and economy of use, and their portability for use in the field.

ELISA assays have been developed and used for measuring the amount of SAA in a sample of blood. These same assays, or variations thereof as devised by one skilled in the art, may be used in the assays of the present invention. Such assays are described in detail in the art (e.g., McDonald et al., 1991, supra; Satoh et al., Am. J. Vet. Res. 56: 1286-1291, 1995; Wilkins et al., Clin. Chem. 40: 1284-1290, 1994; Taktak & Lee, J. Immunol. Meth. 136: 11-16, 1991). An exemplary assay is set forth in Example 1.

Hybridization assays to measure the presence and amount of SAA-encoding mRNA in a sample require nucleic acid probes that specifically hybridize with the mRNA encoding one or more SAA isoforms. The availability of amino acid and nucleotide sequence information for a wide variety of SAAs enables the design and production of such probes, according to known methods. In one embodiment, the probes may be designed to hybridize with an mRNA encoding a particular SAA isoform, by choosing segments of the mRNA that are unique to that isoform. In a preferred embodiment, the probes are designed to hybridize to a portion of the SAA-encoding mRNA that is conserved across isoforms, thereby generating a probe that detects a plurality of SAA isoform mRNAs in the test sample.

As is known in the art, suitable hybridization probes comprise single stranded DNA or RNA molecules. Preferably they are between 10 and 200 nucleotides in length, and most preferably between 18 and 100 nucleotides in length. The probes may be synthesized with a detectable label; alternatively, they may be detectably labeled after synthesis. Probes also may be obtained from cloned DNA that encodes SAA.

Methods in which the aforementioned nucleic acids may be utilized as probes for hybridization assays include, but are not limited to: (1) dot blot hybridization; (2) Southern hybridization (3) northern hybridization; and (4) assorted amplification reactions such as polymerase chain reactions (PCR). Preferred for use in the present invention are rapid hybridization assay, such as dot blots or portable PCR-based assays. These assays are suitable for use in a clinical or field environment. Such assays are described in detail in the art (see, e.g., "Current Protocols in Molecular Biology", eds. Frederick M. Ausubel et al., John Wiley & Sons, 1999).

The assays of the invention are of great utility and value in a variety of applications. Focusing on the exemplary embodiment of the inventions, the assays are particularly suitable for use in early and localized detection of mammary inflammation associated with mastitis. Expanding on this utility, the assays can also be used to monitor the therapeutic effectiveness of treatment of mastitis. The treatment may comprise an established treatment. Alternatively, the assays can be used to screen and evaluate the effectiveness of novel therapeutic agents and treatment regimens. In this embodiment, the milk of control and test animals (subjected to the new treatment or agent) are assayed for the presence and amount of SAA. A decrease in SAA in the test sample, as compared to the control sample, is indicative that the new therapeutic agent or treatment is effective in controlling the inflammation.

The assays described above also may be used to determine if a therapeutic or other agent applied to udder tissue causes any detrimental inflammatory side effects. In this embodiment, as above, milk samples from test animals receiving the treatment is compared with milk samples from control animals for the presence and amount of SAA. In this embodiment, an increase in SAA level in the test samples as compared to the control sample indicates that the treatment has a detrimental inflammatory side effect.

The assays of the invention also may be used to monitor milk quality. A current practice in many parts of the world is to assign a quality rating to a milk batch. Thus, a batch of milk being sold by a farmer is currently assessed for quality by measuring the number of somatic cells present in a sample of the milk, which is correlated with the prevalence of clinical and sub-clinical mastitis in the dairy herd. The assays of the present invention provide a rapid, convenient alternative to the somatic cell measurement to evaluate the quality of a batch of milk.

As another useful embodiment, since SAA is elevated in colostrum and not in milk from normal breast tissue, the measurement of SAA in a milk sample can be used to differentiate colostrum from milk. Accordingly, in instances where it is undesirable to have milk that contains colostrum (some countries have laws to this effect), the methods of the invention may be used to detect colostrum-tainted milk.

The following examples are provided to describe the invention in greater detail. They are intended to illustrate, not to limit, the invention.

EXAMPLE 1

Immunoassay for SAA

1. Preparation of Microtiter Plate:

96-well microtiter plates were prepared by incubating each well with 100 µl of rat monoclonal antibody to bovine SAA (titer=5.0 µg/ml) in carbonate buffer (0.015 M $Na_2CO_3$, 0.035 M $NaHCO_3$ and a pH of 9.6). This plate coating antibody is designated C-100-8. Plates were incubated for 12 hours at 4° C. then the antisera solution is aspirated and the plates washed by filling and emptying all wells 4 times with PBS-Tween which consists of 0.05% v/v Tween 20 (polyoxyethylene sorbitan monolaurate) in phosphate buffered saline (PBS=0.010 M $Na_2HPO_4.2H_2O$, 0.003 M $KH_2PO_4$, 0.132 M NaCl, pH of 7.2). Plates were treated with StabilCoat (SurModics Inc., Eden Prairie, Minn.) for 1 hour at 22° C., dried for 8 hours at 37° C., then sealed in foil bags.

2. Reference Standard:

A solution containing known standard concentration of bovine SAA at 37.5 ng/ml was further diluted two-fold serially 6 times in PBS-Tween. Fifty microliters (50 µl) of the standard and each of the subsequent 6 serial dilutions were used on the plate to establish a standard curve. The standard contained 37.5 ng/ml and the subsequent two-fold dilutions contained 18.8, 9.4, 4.7, 2.3, 1.20 and 0.60 ng/ml, respectively. Fifty µl of PBS-Tween without SAA established background readings.

3. Assay Procedure (Standard Sandwich ELISA):

a. Wells were washed three times with PBS-Tween wash buffer. After the last wash, wells were patted dry on absorbent paper.

b. 50 µl of biotinylated rat monoclonal antibody were added to bovine SAA (1 µg/ml) to each well. This antibody is designated C-100-7 and has a different epitope specificity for SAA than the plate-coating antibody.

c. Serum, colostrum or milk samples were at room temperature and were vortexed vigorously before dilutions were made. Samples were diluted 1:500. In some instances, samples may require greater dilution to fall within the range of the assay. 50 µl of the diluted sample or standard was added to each well. Sides of the plate were tapped to mix gently.

d. The plate was covered with a dust cover, and incubated for 1 hr at 37° C.

e. After incubation, the plate was aspirated or decanted, then washed three times with PBS-Tween buffer. After the last wash, the plate was patted dry on absorbent paper.

f. 100 µl of streptavidin-peroxidase (100 ng/ml) was added to each of the wells.

g. The plate was covered and incubated at room temperature in the dark for 30 minutes.

h. The wells were aspirated or decanted, then washed three times with PBS-Tween, and the plate patted dry after the last wash.

i. 100 µl of substrate consisting of 3,3',5,5'-tetramethyl benzidine at 10 µg/ml (0.1 mg dissolved in 0.1 ml of dimethylsulfoxide and 9.9 ml of 0.1 M sodium acetate pH 6.0 added) was added.

j. The plate was covered and incubated in the dark at room temperature for 30 minutes.

k. 50 µl of a Stop Solution of $H_2SO4$ (prepared by adding 2.8 ml of concentrated $H_2SO4$ to 97.2 ml of water) was added.

l. The absorbance of each well was read at 450 nm having blanked the plate reader against a chromagen blank composed of 100 µl of TMB substrate and 50 µl Stop Solution only.

m. The absorbance of the standards was plotted against standard concentration on graph paper. The background absorbance for the 0 ng/ml may be subtracted from each of the data points, including the standards, unknowns and controls prior to plotting.

n. The concentrations of the test samples and controls was determined from the standard curve by multiplying the interpolated value by the appropriate dilution factor (e.g., colostrum or milk diluted 500 should be multiplied by 500). Samples which have a signal greater than the highest standard were further diluted in diluent buffer and re-analyzed.

EXAMPLE 2

Evaluation of SAA in Colostrum and Subsequent Serial Samplings of Milk

The purpose of this study was to evaluate colostrum and subsequent serial milk samplings to determine SAA content. Samples were obtained from Holstein dairy cows at the University of Nebraska—Lincoln Dairy Research Facility. Samples of colostrum were taken at calving, and subsequent milk samples were taken twice weekly for three weeks. Samples from all four udder quadrants were pooled. Results are shown in Table 2.

TABLE 2

SAA Levels in Colostrum and Milk Samples

| Cow ID | Sample Day | SAA ug/ml |
|---|---|---|
| 83 colostrum | Calving | 184.8 |
| 83 milk | +4 | 0.2 |
| 83 milk | +7 | 0.0 |
| 83 milk | +11 | 0.0 |
| 83 milk | +14 | 0.0 |
| 83 milk | +18 | 0.0 |
| 83 milk | +21 | 0.0 |
| 932 colostrum | Calving | 566.2 |
| 932 milk | +4 | 229.8 |
| 932 milk | +7 | 217.7 |
| 932 milk | +11 | 169.0 |
| 932 milk | +14 | 6.4 |
| 932 milk | +18 | 5.8 |
| 932 milk | +21 | 26.0 |
| 908 colostrum | Calving | 135.6 |
| 908 milk | +4 | 2.6 |
| 908 milk | +7 | 9.1 |
| 908 milk | +11 | 8.2 |
| 908 milk | +14 | 2.0 |
| 908 milk | +18 | 2.1 |
| 908 milk | +21 | 3.6 |
| 961 colostrum | Calving | 364.6 |
| 961 milk | +4 | 0.3 |
| 961 milk | +7 | 0.5 |
| 961 milk | +11 | 0.0 |
| 961 milk | +14 | 0.0 |
| 961 milk | +18 | 0.0 |
| 961 milk | +21 | 0.0 |

The results obtained above for cows 83, 908 and 961, each of which was free of mastitis in all quadrants, shows the low basal level of SAA present in normal milk samples after colostrum has cleared.

The results obtained for cow 932 demonstrates that SAA level can effectively detect mastitis in a quadrant specific manner. Midway through the sampling period, cow 932 was observed to be symptomatic for mastitis in one quadrant. Even though all four quadrants' milk were pooled in the first three milk samplings, the samples were elevated in SAA. In the subsequent samplings, the mastitis quadrant was not milked, so was not pooled with the milk from the unaffected quadrants. As a result, SAA levels decreased in those samples to approximately the levels observed in the completely asymptomatic cows.

EXAMPLE 3

SAA Levels as a Quadrant-Specific Indicator of Mastitis

The purpose of this study was to determine if SAA can detect mastitis-related inflammation, and if SAA is elevated only in the affected quadrant, or in milk from all quadrants.

Samples were obtained from the Holstein dairy herd at the University of Nebraska—Lincoln Dairy Research Facility. Three cows with mastitis in the left rear (LR) quadrant of the udder were selected. Each cow was judged visually for the level of inflammation present in each cow. Cow 874 displayed low-grade inflammation, while cow 59 displayed significant inflammation and cow 978 displayed high grade inflammation.

Milk samples were taken from all four quadrants of each cow, and SAA levels were determined by ELISA for the non-pooled samples. Results are shown in Table 3.

TABLE 3

SAA Levels in Milk from Udder quadrants

| Cow ID | Quadrant | SAA (ug/ml) |
|---|---|---|
| 874 | RF | 12 |
| 874 | RR | 10 |
| 874 | LF | 11 |
| 874 | LR (Mastitis) | 73 |
| 59 | RF | 1 |
| 59 | RR | 1 |
| 59 | LF | 7 |
| 59 | LR (Mastitis) | 212 |
| 978 | RF | 6 |
| 978 | RR | 18 |
| 978 | LF | 8 |
| 978 | LR (Mastitis) | 2368 |

The results demonstrate that SAA levels provide a quadrant-specific indicator of inflammation due to mastitis. SAA elevation is confined to the affected quadrant. Moreover, a direct correlation was observed between the visual symptoms of inflammation and SAA levels found in the affected quadrant.

The present invention is not limited to the embodiments described above, but is capable of modification within the scope of the appended claims.

We claim:

1. A method for detecting an inflammatory response in a breast of a lactating mammal, comprising:
   obtaining a milk sample from the breast of a mammal;
   measuring the presence or amount of a Serum Amyloid A (SAA) protein or mRNA encoding the protein from the sample; and,
   correlating the amount of the SAA protein or mRNA encoding the protein present in the sample with mastitis.

2. The method of claim 1, wherein the mastitis is caused by infection with a microorganism.

3. The method of claim 1, wherein the mastitis is caused by a non-infective agent.

4. The method of claim 1, wherein the SAA protein comprises one or more inflammation-responsive isoforms of SAA.

5. The method of claim 4, wherein the SAA protein comprises an amino acid sequence selected from the group consisting of SEQ ID NO:1.

6. The method of claim 1, wherein the amount of SAA protein is measured using an immunological assay with antibodies immunologically specific for one or more isoforms SAA.

7. The method of claim 6, wherein the immunological assay is an ELISA assay.

8. The method of claim 1, which comprises measuring the amount of SAA mRNA encoding the protein in the milk sample.

9. The method of claim 8, wherein the amount of SAA mRNA is measured using a hybridization assay with nucleic acid molecules complementary to the SAA mRNA encoding the protein in the sample.

10. A method for detecting mastitis in a breast of a lactating mammal, comprising:
    obtaining a milk sample from the breast of a mammal;
    measuring the presence or amount of a Serum Amyloid A (SAA) protein or mRNA encoding the protein from the sample, wherein the SAA protein is an amino acid sequence set forth as SEQ ID NO:1; and
    correlating the amount of the SAA protein or mRNA encoding the protein present in the sample with mastitis.

* * * * *